United States Patent [19]

Kim et al.

[11] Patent Number: 5,929,262
[45] Date of Patent: Jul. 27, 1999

[54] METHOD FOR PREPARING 17α-ACETOXY-11β-(4-N, N-DIMETHYLAMINOPHYL)-19-NORPREGNA-4,9-DIENE-3, 20-DIONE, INTERMEDIATES USEFUL IN THE METHOD, AND METHODS FOR THE PREPARATION OF SUCH INTERMEDIATES

[75] Inventors: Hyun K. Kim, Bethesda, Md.; Pemmaraju Narasinha Rao, San Antonio; James E. Burdett, Jr., Somerset, both of Tex.; Carmie K. Acosta, San Antonio, Tex.

[73] Assignee: The United States of America as represented by the Department of Health and Human Services, Washington, D.C.

[21] Appl. No.: 08/413,755

[22] Filed: Mar. 30, 1995

[51] Int. Cl.[6] .............................. C07J 75/00; C07J 7/00
[52] U.S. Cl. ............................................................ 552/598
[58] Field of Search .............................................. 552/598

[56] References Cited

U.S. PATENT DOCUMENTS

| | | |
|---|---|---|
| 3,872,092 | 3/1975 | Teustsch et al. . |
| 4,147,695 | 4/1979 | Teutsch . |
| 4,233,296 | 11/1980 | Teutsch et al. . |
| 4,386,085 | 5/1983 | Teutsch et al. . |
| 4,447,424 | 5/1984 | Teutsch et al. . |
| 4,477,445 | 10/1984 | Philibert et al. . |
| 4,519,946 | 5/1985 | Teutsch et al. . |
| 4,536,401 | 8/1985 | Neef et al. . |
| 4,547,493 | 10/1985 | Teutsch et al. . |
| 4,548,748 | 10/1985 | Van Rheenen ............... 260/239.55 |
| 4,585,590 | 4/1986 | Van Rheenen ............... 260/239.55 |
| 4,634,695 | 1/1987 | Torelli et al. . |
| 4,720,357 | 1/1988 | Tchernatinsky . |
| 4,780,461 | 10/1988 | Neef et al. . |
| 4,831,131 | 5/1989 | Van Rheenen ..................... 540/87 |
| 4,921,638 | 5/1990 | Livingston et al. . |
| 4,954,490 | 9/1990 | Cook et al. . |
| 4,977,255 | 12/1990 | Livingston et al. . |
| 5,003,063 | 3/1991 | Reid . |
| 5,073,548 | 12/1991 | Cook et al. . |
| 5,149,696 | 9/1992 | Claussner et al. . |
| 5,260,463 | 11/1993 | Brion et al. . |
| 5,272,140 | 12/1993 | Loozen . |
| 5,273,971 | 12/1993 | Scholz et al. . |
| 5,290,771 | 3/1994 | Claussner et al. . |
| 5,332,847 | 7/1994 | Hempel . |
| 5,401,840 | 3/1995 | Brion et al. . |
| 5,502,182 | 3/1996 | Brion et al. . |
| 5,556,962 | 9/1996 | Brion et al. . |

FOREIGN PATENT DOCUMENTS

| | | |
|---|---|---|
| 2 146 600 | 9/1995 | Canada . |
| 0 268 400 | 5/1988 | European Pat. Off. . |
| 0268400 | 5/1988 | European Pat. Off. . |
| 0 531 212 | 3/1993 | European Pat. Off. . |
| 0 676 203 | 10/1995 | European Pat. Off. . |
| 2 201 287 | 4/1974 | France . |
| 2201287 | 4/1974 | France . |
| 2 215 416 | 8/1974 | France . |
| WO 89/12448 | 12/1989 | WIPO . |

OTHER PUBLICATIONS

Teutsch et al., "Synthesis of the 10beta–ethynyl analogue of hydrocortisone acetate". J. Chem. Res., p. 87, 1981.

National Institutes of Health, "Sources sought annoucement" dated Jun. 14, 1993, with attached synthetic scheme.

Commerce, "Business Day" dated Jun. 15, 1993, (Issue No. PSA0867).

National Institutes of Health "Sources Sought Annoucement" dated Jun. 14, 1993 with attached synthetic scheme for "17α–Acetoxy–11β–(4–N, N–Dimethylaminophenyl)–19–Norpregna–4,9–Diene–3, 20–Dione".

(List continued on next page.)

*Primary Examiner*—Jose G. Dees
*Assistant Examiner*—Barbara Badio
*Attorney, Agent, or Firm*—Leydig, Voit & Mayer

[57] ABSTRACT

Methods for the preparation of the 19-norprogesterone of formula I

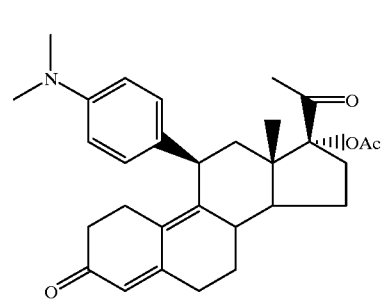

(I)

and its intermediates, in crystalline and amorphous forms are disclosed. The process is performed by (1) protecting the hydroxyl group of a compound of formula II

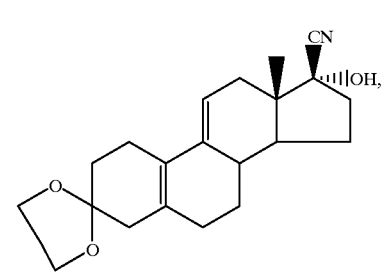

(II)

(2) reacting the protected compound with an alkali or alkaline earth metal anion radical, (3) hydrolyzing the resulting compound, (4) ketalizing the carbonyl groups, (5) epoxidizing the compound, (6) opening the epoxide ring and introducing an N,N,dimethylamino-phenyl functional group into the axial position of $C_{11}$, (7) deketalizing and dehydrating the resulting compound, and (8) acetylating to provide 17α-acetoxy-11β-(4-N,N-dimethylaminophenyl)-19-norpregna-4,9-diene-3,20-dione (I).

19 Claims, 2 Drawing Sheets

OTHER PUBLICATIONS

Teutsch et al., "Regioselective Base–catalysed Rearrangement of Steroidal αβ–Unsaturated Epoxides", *J. Chem. Soc., Chem. Comm.*, No 18, (1974), pp. 763–764.

Teutsch et al., "Synthesis of the 10β–Ethynyl Analogue of Hydrocortisone Acetate" *J. Chem. Res.*, (1981), p. 87.

Suming et al., "Stereoselective Epoxidation of 5(10)–ENE of 11β–Functionated Steroids and Effect of (10)–Epoxy Group on Reaction of 11β–Substitute" *Heterocycles*, 40, (1), (Jan. 1995), pp. 205–212.

Acosta et al., "Oxidative Demethylation of 4–Substituted N,N–Dimethylanilines with Iodine and Calcium Oxide in the Presence of Methanol" *J. Chem. Soc., Chem Comm.*, No. 17, (1994), pp. 1985–1986.

Wang et al., "The Anti–Progestin CDB 2914 Has No Antifertility Effect in Male Rats" *Contraception*, 51, (3), (Mar. 1995), pp. 215–218.

Poyser et al., "A Comparison of the Pregancy–Terminating Potencies of Three Anti–Progestins in Guinea–Pigs, and the Effects of Sulprostone" Prostaglandins, Leukotrienes Essential Fatty Acids, 50, (5), (1994), pp. 245–247.

Cook et al., "Reversal of Activity Profile in Analogs of the Antiprogestin RU 486: Effect of a 16α–Substituent on Progestational (Agonist) Activity" *Life Science*, 52, No. 2, (1993), pp. 155–162.

International Search Report for International Application PCT/US96/03660 dated Oct. 31, 1996.

Cook et al., "Effects of D–ring substituents on antiprogestational (antagonist) and progestational (agonist) activity of 11β–aryl steroids" 9 *Human Reproduction*, 32–39 (Suppl. I, 1994).

Rao et al., "Synthesis of [13]C–Labelled Medroxyprogesterone Acetate with Three [13]C Isotopes [1]" *XIX, (3), J. Labelled Compounds and Radiopharmaceuticals*, 363–372 (1982).

Large Scale Synthetic Process for the Preparation of 17a–Acetoxy–11B–(4–N, N–Dimethylaminophenyl)–19–Norpregna–4–Diene–3, 20–Dione.

Application of Silicon Chemistry in the Corticosteroid Field. Advances in Medicinal Chemistry, vol. 1, pp. 137–174 (1992) Livingston.

Intramolecular Cyanohydrin Elaboration. Construction of Corticosteroids from 17–Ketosteroids. J. Am. Chem. Soc. 1990, 112, 6449–6450.

Alkyllithium Reagents form Alkyl Halides and Lithium Radical anions. J. Org. Chem., 45, 1924–1930 (1980).

Cleve, et al, Tetrahedron, 49(11), 2217–26 (1993).

Claussner, et al, J. Ster Biochem & Mol. Biol, 41(3–8), 609–14 (1992).

Smid, et al, Analyst, 119, pp. 2645–50(1994).

Kasal, et al, Collect Czech. Chem. Commun, 58, pp. 619–628 (1993).

Numaza, et al, et al, J. Med. Chem, 37, pp. 1312–1319 (1994).

5,929,262

1

METHOD FOR PREPARING 17α-ACETOXY-11β-(4-N, N-DIMETHYLAMINOPHYL)-19-NORPREGNA-4,9-DIENE-3, 20-DIONE, INTERMEDIATES USEFUL IN THE METHOD, AND METHODS FOR THE PREPARATION OF SUCH INTERMEDIATES

TECHNICAL FIELD OF THE INVENTION

The present invention relates generally to steroids and, in particular, to methods for the preparation of 17α-acetoxy-11β-(4-N,N-dimethylaminophenyl)-19-norpregna-4,9-diene-3,20-dione, intermediates useful in those methods, and methods for the preparation of such intermediates.

BACKGROUND OF THE INVENTION

The compound 17α-acetoxy-11β-(4-N,N-dimethylaminophenyl)-19-norpregna-4,9-diene-3,20-dione, represented by formula I

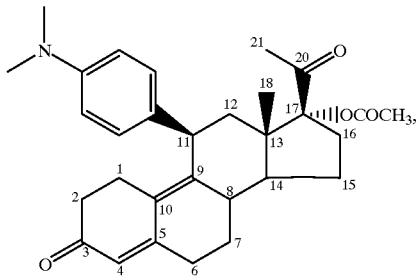

is a well-known steroid, more specifically a 19-norprogesterone, which possesses antiprogestational and antiglucocorticoidal activity. This compound, and a method for its preparation, are described in U.S. Pat. No. 4,954,490.

The method for the preparation of the 19-norprogesterone compound of formula I set forth in the '490 patent is reproduced in FIG. 1. This method begins by converting 3-methoxyesterone 1 to a tetra-ene 2 via the Wittig reaction using ethyl triphenyl phosphonium iodide. The tetra-ene 2 is then hydroxylated using $OsO_4$ to provide the compound of formula 3. That compound is then reduced using $Li/NH_3$ to form compound 4, with the latter being subjected to mild acid hydrolysis to form compound 5. Subsequently, compound 5 is subjected to bromination-dehydrobromination to provide a dienone 6. Swern oxidation is then used to convert the dienone 6 to compound 7, with compound 7 being ketalized to provide a ketal 8. The ketal 8 is then epoxidized using m-chloroperbenzoic acid to provide an epoxide 9. The epoxide then undergoes conjugate ring-opening using a copper (I) catalyzed Grignard reagent generated by the reaction of 4-bromo-N,N dimethylaniline with magnesium in the presence of copper (I) to provide compound 10. A single-step hydrolysis/acetylation/dehydration procedure, using $H_3PO_4/Ac_2O/HOAc$, is then used to convert compound 2- to the desired 19-norprogesterone of formula I (indicated as compound 11 in FIG. 1).

While the foregoing procedure can be used to provide the 19-norprogesterone of formula I, certain drawbacks are inherent therein. More specifically, the foregoing procedure includes processing steps which are hazardous and/or not readily amenable to the preparation of relatively large quantities of the desired 19-norprogesterone, e.g., the use of highly toxic and expensive $OsO_4$ to affect hydroxylation, effecting Birch reduction using lithium and ammonia, as

2 well as bromination-dehydrobromination and Swern oxidation procedures. Moreover, many of the steps require chromatographic purification for the isolation of the intermediates. Further, the overall yield provided by this known process is relatively low.

In view of the foregoing, a need exists for a relatively safer and more efficient process for the preparation of the 19-norprogesterone of formula I and intermediates thereof, which process is further able to provide those compounds in relatively high quantities and purity levels, as compared to known methods. These and other objects and advantages of the present invention, as well as additional inventive features, will be apparent from the description of the invention provided herein.

BRIEF SUMMARY OF THE INVENTION

One aspect of the present invention provides methods for the preparation of the 19-norprogesterone of formula I and its intermediates which are relatively safer and more efficient, and which further provide those compounds in relatively high quantities and purity levels, as compared to known methods.

With respect to the preparation of the 19-norprogesterone of formula I, the present invention comprises protecting the hydroxyl group in the compound of formula II

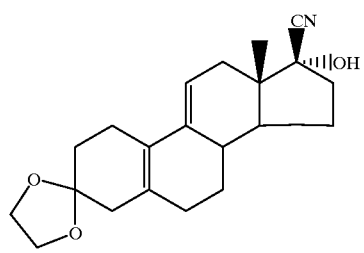

with a protecting group B, which protecting group comprises a halomethyl functional group, to provide the compound of formula III

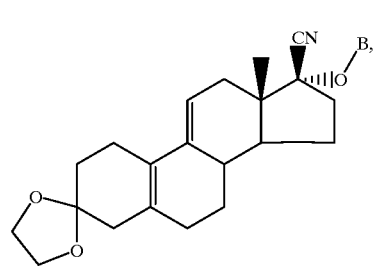

reacting the protected compound of formula III with an alkali or alkaline earth metal anion radical comprised of an alkali or alkaline earth metal and an anion radical and hydrolyzing the resulting compound to provide the compound of formula IV

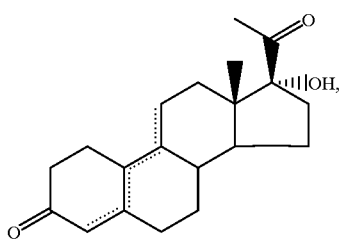

(IV)

ketalizing the carbonyl groups of the compound of formula IV to provide the compound of formula V

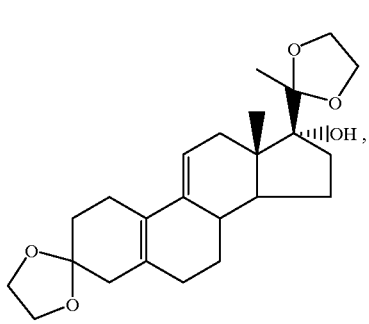

(V)

epoxidizing the compound of formula V to provide the 5α,10α-epoxide compound of formula VI

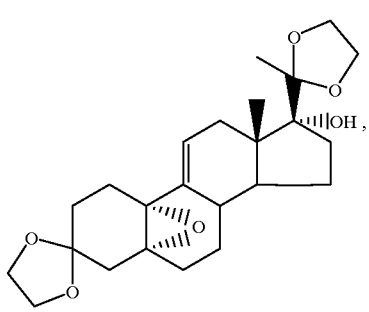

(VI)

opening the epoxide ring in the compound of formula VI and substituting a N,N-dimethylaminophenyl functional group in the axial position of $C_{11}$ to provide the compound of formula VII

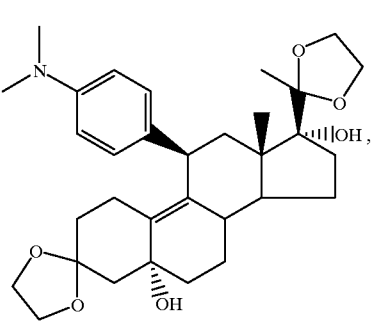

(VII)

deketalizing and dehydrating the compound of formula VII to provide the compound of formula VIII

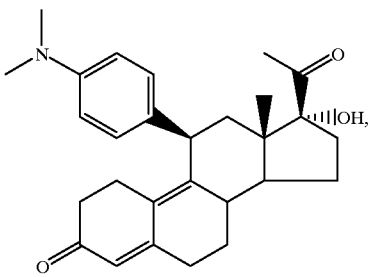

(VIII)

and acetylating the compound of formula VIII to provide the compound of formula I.

By following the foregoing method, one is able to avoid using the hazardous bromination-debromination and Swern oxidation procedures and, further, is able to obtain the desired 19-norprogesterone in a relatively high yield and purity level.

As mentioned previously, another aspect of the present invention provides methods for the preparation of several of the intermediates useful in the foregoing method for the preparation of the 19-norprogesterone of formula I.

Yet another aspect of the present invention provides crystalline forms of the 19-norprogesterone of formula I, as well as certain of the aforesaid intermediates, i.e., the compounds of formulas V, VI, VII, and VIII, as well as of IIIa (which is formula III in which B is —Si(CH$_3$)$_2$CH$_2$Cl)

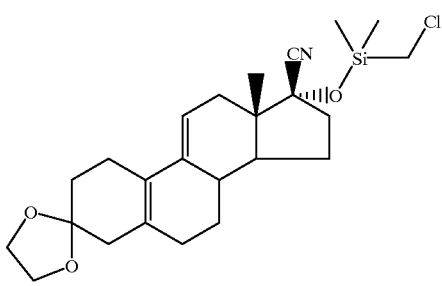

(IIIa)

DESCRIPTION OF THE PREFERRED EMBODIMENTS

Figure 1:
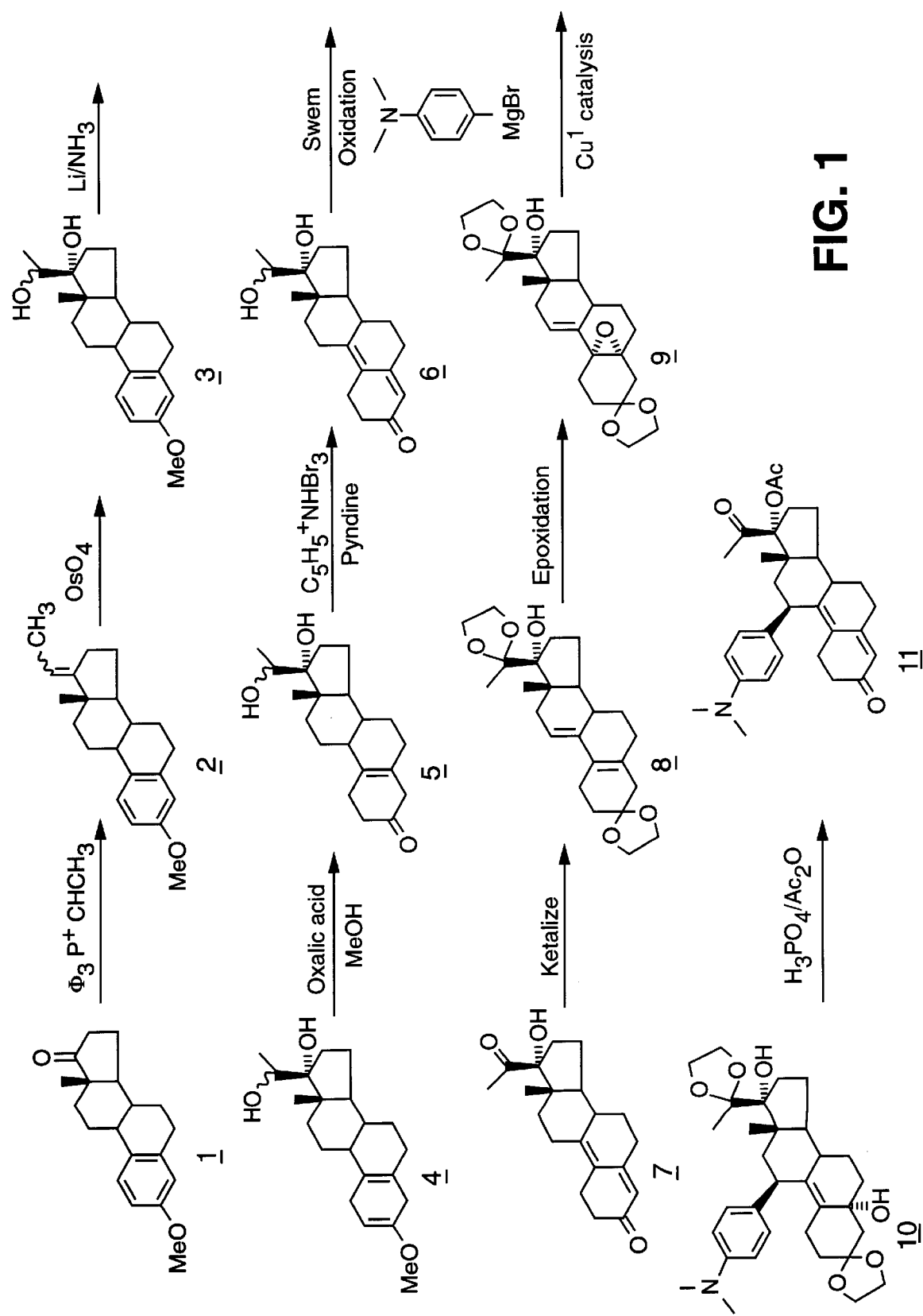
FIG. 1 sets forth the method for the preparation of the 19-norprogesterone of formula I (indicated in this figure as the compound of formula 11) as described in U.S. Pat. No. 4,954,490.

The invention may best be understood with reference to the following detailed description of the preferred embodiments.

One aspect of the present invention provides a method for preparing the compound of formula I

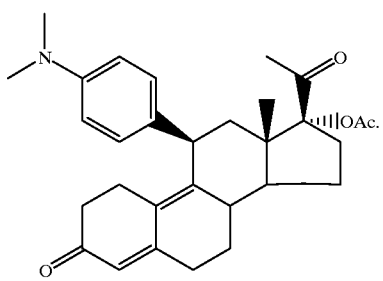

(I)

Prior to initiating the inventive method, the starting material, i.e., the compound of formula II

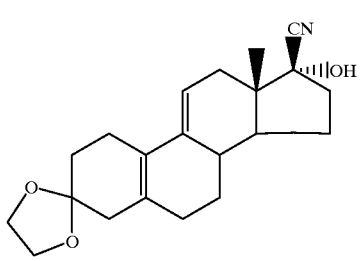

(II)

must be obtained. This compound is commercially available from Roussel-Uclaf (Paris, France).

As an initial step, the hydroxyl group in the compound of formula II is protected by the addition of a protective group to form the compound of formula III

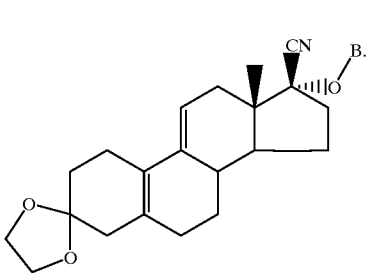

(III)

While any suitable protecting group having a halomethyl functional group may be utilized, it has been advantageously found that a silane radical (—Si(CH$_3$)$_2$CH$_2$X, wherein X is Cl, Br or I), and preferably (because it is the least costly of the three radicals) the radical formed from chloromethyldimethylchlorosilane (i.e. —Si(CH$_3$)$_2$CH$_2$Cl), provides certain benefits, e.g., each may be readily generated from commercially available materials.

When the preferred protecting group is used, the reaction preferably proceeds by reacting the compound of formula II with that protecting group in a suitable anhydrous solvent. Examples of solvents suitable for this reaction include, but are not limited to, tetrahydrofuran (THF), diethyl ether, acetonitrile, dichloromethane, dioxanes and the like, with THF being a preferred solvent.

The protecting reaction is preferably further conducted in the presence of a bases the base functioning to scavenge the acid by-product. Examples of suitable bases include triethylamine and pyridine.

Most preferably, the protecting reaction is further conducted in the presence of a silylation catalyst, e.g., 4-N,N-dimethylaminopyridine (DMAP), which is typically present in a substoichiometric amount.

During the reaction, the reactants are advantageously maintained at a temperature of from about 0° C. to about 40° C., and preferably at a temperature of about 25° C. When the reaction is complete, the reaction mixture is diluted with a non-polar solvent or mixture of such solvents, e.g., pentanes and hexanese to precipitate the amine hydrochloride byproduct. The precipitate may then be removed by any known method, e.g. filtration. The filtrate may then be concentrated by evaporation, and subsequently diluted with a solvent, e.g., diethyl ether, in order to be able to subject it to further purification. It is preferred that the solution be kept under a dry atmosphere, such as a nitrogen atmosphere. The solution is then preferably passed through a silica gal column to obtain the compound of formula IIIa (assuming the protecting group is —Si(CH$_3$)$_2$CH$_2$Cl) as a crystal (m.p. 80° to 82° C.) in 98% yield.

The protected compound of formula III is then reacted in a single-step with an alkali or alkaline earth metal anion radical comprised of an alkali or alkaline earth metal and a radical anion. It is believed that, during the reaction, the nucleophilic carbon atom of the halomethyl functional group in the protecting group intramolecularly attacks the nitrile group and forms a cyclic structure therewith. Therefore, selection of the alkali or alakaline earth metal anion radical should be based upon the ability of the radical to initiate the aforementioned intramolecular attack. Examples of suitable alkali metals that can be used in the practice of the present invention include lithium, sodium, potassium, and rubidium, with lithium being preferred. Calcium is a preferred alkaline earth metal. Examples of compounds suitable for forming the radical anion include naphthalene, di-tert-butylnaphthalene, di-tert-butylbiphenyl (DBB), anthracene, naphthacene, benzanthrene, benzophenone, 1,3,5-trinitrobenzene, dimethylaminonaphthalene, diisopropylamide, hexamethyl phosphoric triamide, ammonia, and 18-crown-6. The use of DBB is preferred in view of its high efficiency in generating the anion radical. See Freeman et al., *J. Org. Chem.* 45, 1924–1930 (1980).

The resulting reaction mixture, which includes the aforedescribed compound having the two cyclic structures, i.e., the cyclic ketal group and the cyclic structure formed by the previously described intramolecular attack, is then quenched with an excess of acid, advantageously an aqueous acid, and the compound having the said two cyclic structures is concomitantly hydrolyzed, to provide the compound of formula IV

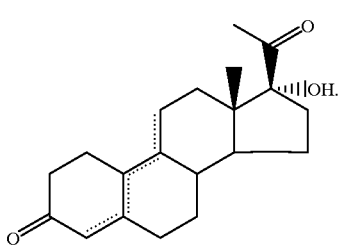

(IV)

Preferably, the aforesaid resulting reaction mixture is quenched with CH$_2$Cl$_2$ to destroy any excess alkali metal or alkaline metal anion radical present in that mixture prior to the acid quenching step.

When the preferred compound is used in the foregoing reaction sequence, i.e., DBB, the reaction of the alkali metal with DBB is preferably conducted in the presence of a solvent, e.g., THF. As the alkali metal/DBB complex is highly sensitive to oxygen and moisture, care should be exercised in handling this complex. Subsequently, the alkali metal/DBB complex is reacted with the compound of formula III.

The reactants should advantageously be contacted with one another at a low temperature, preferably at about −75° C. to about −30° C., due to the instability of the reaction intermediates.

When the protecting group is the radical —Si(CH$_3$)$_2$CH$_2$X (as described previously), this building of the pregnane side chain is advantageously completed using a single-step procedure known as the Silicon Nucleophilic Annealation Process (SNAP). See Livingston et al., Adv. Med. Chem. 1, 137–174 (1992); Livingston et al., J. Am. Chem. Soc'y 112, 6449–6450 (1990), U.S. Pat. No. 4,921,638; and U.S. Pat. No. 4,977,255. When SNAP is utilized, the compound of formula III (wherein B is —Si(CH$_3$)$_2$CH$_2$X, wherein X is preferably Cl) is reacted with the DBB anion radical generated from DBB and the alkali metal (e.g., lithium) in a solvent, e.g., THF. This results in the formation of an α-silyl carbanion, which attacks the nitrile intramolecularly to provide an intermediate silacycle. Subsequent acid hydrolysis of this intermediate provides the 17α-hydroxy-20-ketone moiety, and concomitant deketalization provides the compound of formula IV.

After the compound of formula IV is prepared, the carbonyl groups of that compound are ketalized to provide the compound of formula V

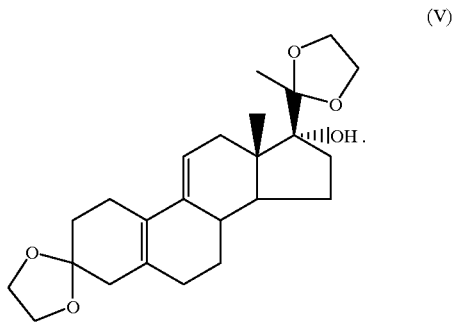

(V)

The ketalization step may be conducted in any suitable manner, but is preferably undertaken by reacting the compound of formula IV with a diol in the presence of an acid.

Any suitable acid may be used in the foregoing reaction, as long as it functions to catalyze the formation of the ketal. Suitable acids for this purpose include sulfur-based organic acids, e.g., methanesulfonic acid, ethanesulfonic acid, benzenesulfonic acid, and naphthalenesulfonic acid, with toluenesulfonic acid being preferred.

Any suitable diol may be used in the reaction, provided that it is able to provide a cyclic ketal. Such diol should further be provided in excess with respect to the carbonyl groups being ketalized, such so as to favor the formation of the cyclic ketal. A preferred diol for this reaction is ethylene glycol.

Various orthoesters are suitable for use in the foregoing reaction, the orthoesters functioning to chemically remove the water from the reaction and drive the reaction to comple tion. Orthoformate esters are advantageously utilized because they provide high yields. Preferred orthoformateesters include triisobutyl orthoformate and triisopropyl orthoformate, with triethyl orthoformate being most preferred.

The compound of formula V is then epoxidized to form the 9,11-unsaturated 5α,10α-epoxide of formula VI

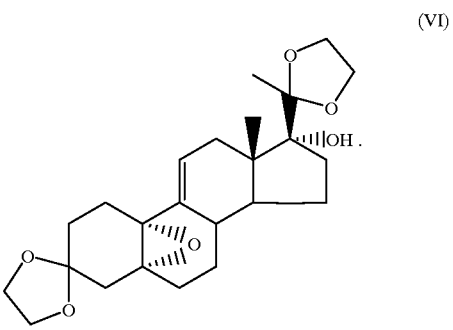

(VI)

This reaction is advantageously accomplished by reacting the compound of formula V with an adduct formed from the reaction of a halogenated acetone and a peroxide in the presence of an inorganic phosphate. Any suitable peroxide, or peracid, may be used in this reaction. Examples of suitable peroxides include hydrogen peroxide sodium peroxide potassium peroxide, benzoyl peroxide, and acetyl peroxide, with the preferred peroxide being 30 wt. % hydrogen peroxide in water.

The halogenated acetone may comprise any such acetone which provides the desired results. Advantageously, a hexahalogenated acetone is used, e.g., hexafluoroacetone, hexachloroacetone and hexabromoacetone, with hexafluoroacetone being preferred. Such hexahalogenated acetones provide the 5α,10α-epoxide in the greatest yield.

The reaction is preferably carried out in the presence of an inorganic bases Examples of suitable bases include di- and tri-basic sodium and potassium phosphate, sodium and potassium carbonate, and sodium and potassium bicarbonate, with dibasic sodium phosphate being preferred. Especially preferred is the use of dibasic sodium phosphate in combination with the 30 wt. % hydrogen peroxide and hexafluoroacetone.

The reaction is further advantageously conducted in the presence of a solvent. The solvent should advantageously be a halogenated solvent. Suitable solvents include chloroform, methylene chloride, dichloroethane, and trichloroethane, with a preferred solvent being methylene chloride.

The compound of formula VI can be crystallized (m.p. 188.5° C. to 191.5° C.) using an ether, e.g., diethyl ether, isopropyl ether, isobutyl ether, and n-butyl ether, with diethyl ether being preferred.

After forming the cyclic ketal protecting groups, the epoxide in the compound of formula VI, advantageously in its crystalline form, undergoes a conjugate ring-opening reaction, and a N,N-dimethylaminophenyl functional group may be substituted in the axial position of C$_{11}$, to provide the compound of formula VII

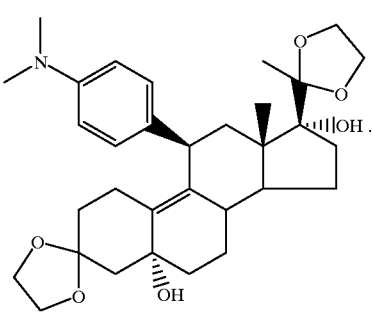

(VII)

The foregoing reaction is advantageously completed by reacting the crystalline compound of formula VI with a Grignard reagent prepared from the reaction of p-bromo-N,N-dimethylaniline and magnesium in the presence of a cuprous halide.

It was surprisingly discovered that, when this reaction scheme was undertaken, less Grignard reagent was required as compared to the amount of such agent required in the conversion of the unpurified product. More specifically, the reaction may be carried out with about a five-fold excess of Grignard reagent over the epoxide as opposed to the nearly eight-fold excess used in the process described in the '490 patent.

The crystalline form of compound VI further permits the use of a relatively small amount of the cuprous halide reagent. More specifically, the conjugate ring opening reaction of the 5α,10α-epoxide can be carried with the molar ratio of the cuprous halide to the 5α,10α-epoxide at about one-half; this being contrasted with the more than equimolar quantity of cuprous reagent described in the '490 patent.

It was further surprisingly discovered that the use of the crystalline form of compound VI, while using a relatively small amount of reagents (e.g., Grignard and cuprous halide), provided the compound of formula VII in high yield and purity, without requiring purification to be undertaken by means of time-consuming chromatographic methods.

Compound VII is further advantageously obtained in crystalline form (m.p. 236° C. to 240° C.) by crystallization from an ether, preferably, diethyl ether.

The compound of formula VII, advantageously in its crystalline form, is then deketalized and dehydrated to provide the compound of formula VIII

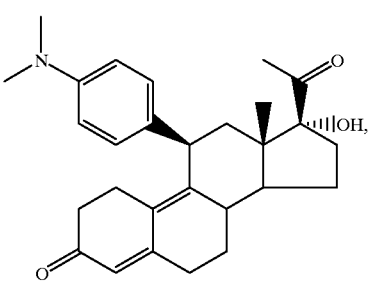

(VIII)

wherein thereafter the compound of formula VIII is acetylated to provide the compound of formula I.

The foregoing conversion of the compound of formula VII to the compound of formula I is completed by carrying out the conversion in two steps. This two-step procedure is in direct contrast to the one-step procedure described in the '490 patent. More specifically, the first step comprises the conversion of the compound of formula VII to the compound of formula VIII by reaction with a dilute alcoholic acid solution. The acid serves the dual function of hydrolyzing the ketal group (i.e., deketalization) and removing the hydroxyl at $C_5$ position (i.e., dehydration). Any acid which functions to hydrolyze the ketal group is suitable for use, including sulfuric acid, hydrochloric acid, and phosphoric acid.

After its formation, the compound of formula VIII may be crystallized (m.p.: softens at 103° C. and foams at 125° C. to 128° C.) from ether in high yield and in high purity. The compound of formula I may then be prepared from the compound of formula VIII, advantageously its crystalline form, by acetylation. Although any suitable reactants may be utilized to complete the acetylation, advantageously, a mixed anhydride procedure employing a trifluoroacetic anhydride/acetic acid mixture is used. This procedure has been found to provide the compound of formula I in high purity and yield from the compound of formula VIII without resort to chromatography. After its formation, the compound of formula I can be purified by crystallization from ether in high yield and high purity (m.p.: 183° C. to 185° C.).

The inventive method for preparing the compound of formula I from the compound of formula VII in two steps was surprisingly found to provide a greater yield of the desired product than the one step method described in the '490 patent, i.e., a net yield of about 68% as compared to about 16% as calculated from the yields reported in the '490 patent.

Figure 2:
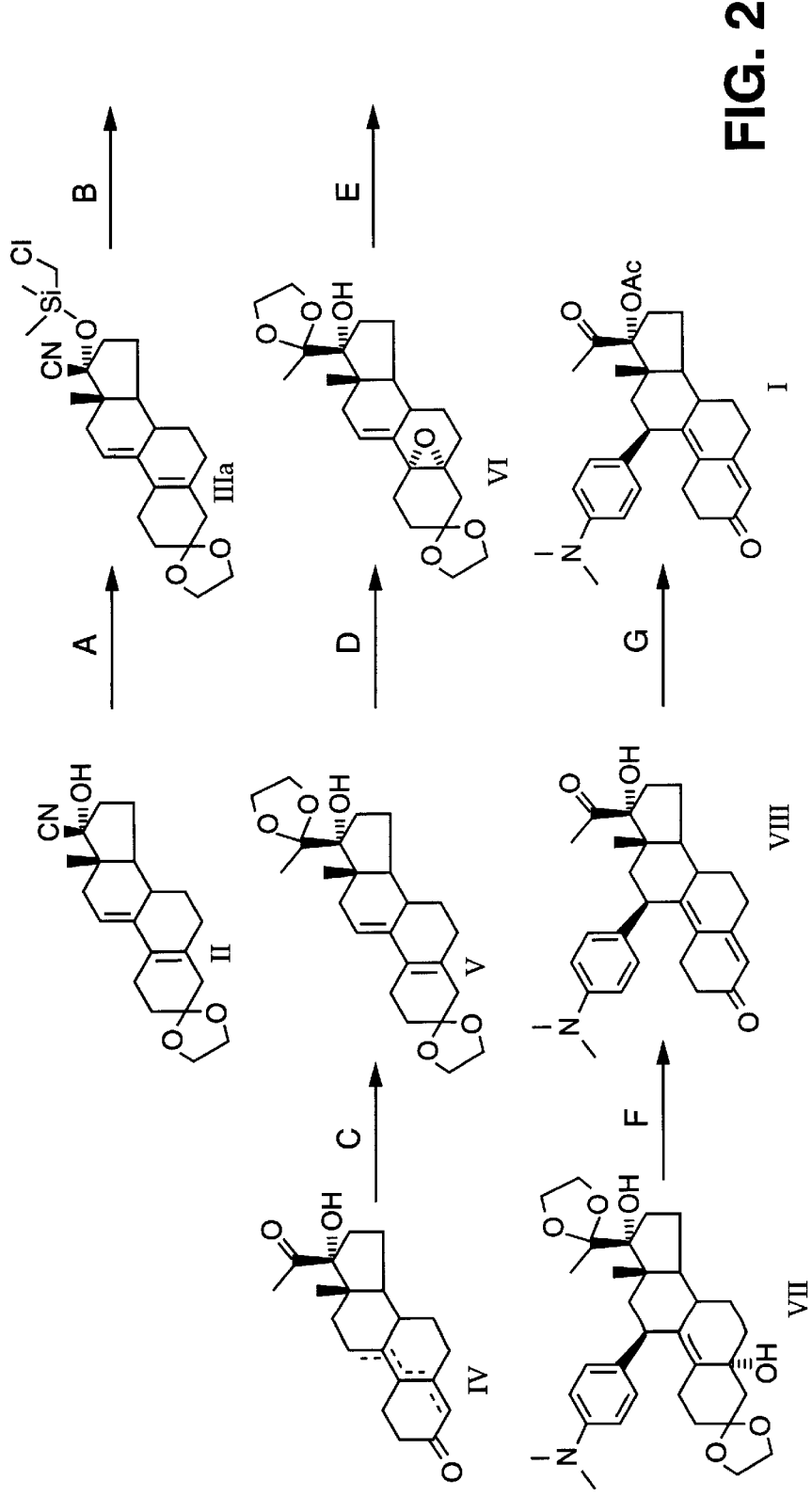
FIG. 2 sets forth the method for the preparation of the 19-norprogesterone of formula I in accordance with the present invention.

From an overall perspective, the inventive method provides a much greater yield of the final product of formula I as compared to that provided by the '490 patent, and also avoids many of the problems of the reaction scheme described in the '490 patent, such as the use of synthetic procedures which are unreasonably hazardous and/or not readily amenable to scale-up. By following the methods of the present invention, one may obtain an overall yield of the compound of formula I of about 12% starting from compound II. This is contrasted with the nine-step method described in the '490 patent which provides an overall yield of about 0.65% as calculated from the reported yields at the various steps. A preferred embodiment of the present inventive reaction scheme is depicted in FIG. 2.

The instant invention further allows one to prepare any of the intermediates described herein starting from the compound of formula II, or any other preceding intermediate, as well as the compound of formula I starting from any of the aforesaid.

The following examples further illustrate the present invention but, of course, should not be construed as in any way limiting its scope.

EXAMPLE 1

The Preparation of the Compound of Formula (IIIa) (3-ethylenedioxy-17β-cyano-17α-chloromethyl-(dimethyl)silyloxyestra-5(10),9(11)-diene) from the Compound of Formula (II)

700 grams (2.05 mol) of the cyanohydrin-ketal (II) were suspended in about 5,000 mL of anhydrous THF. 58 grams (0.47 mol) of 4-N,N-dimethylaminopyridine were added while maintaining vigorous stirring, followed by the addition of 335 mL (2.40 mol) of triethylamine. 300 mL (2.25 mol) of chloro(chloromethyl)dimethylsilane were added over 15 minutes to the mixture. After stirring for 15 hours at room temperature, the mixture was diluted with 5,000 mL of hexanes and stirred for 10 minutes. The mixture was filtered through a pad of Celite. The filtrate was evaporated, and the residue was taken up in 2,500 mL of ether. This ether solution was percolated under nitrogen through a (15×20 cm) column of pre-equilibrated silica gel (flash column grade) contained in a large flash column (15×70 cm). Evaporation of the ether solution from the column gave 898 g of white crystalline powder (i.e., the compound of formula (IIIa)) in 98% yield; m.p. 80–82° C. The material was found to be homogeneous by Thin Layer Chromatography (TLC) (30% EtOAc/Hex) and was used in the nest reaction without further purification. FTIR (KBr, diffuse reflectance): $v_{max}$ 3034, 2977, 2947, 2865, 2230 (CN), 1546, 1473, 1431, 1383, 1346, 1322, 1256 & 1235 (O—$CH_2CH_2$—O), 1173, 1158, 1131 (Si—O—$CH_2$), 1099, 1058, 1041, 1010 cm$^{-1}$; $^1$H (CDCl$_3$): δ0.47 (s, OSi(CH$_3$)$_2$), 0.90 (s, 18—CH$_3$), 2.88 (s, OSiCH$_2$Cl), 3.99 (br. s, 3—O(CH$_2$)$_2$O—), 5.60 (br. s, C-11 H); HS (EI): m/z (relative intensity) 448(M$^+$, 33), 447(M$^+$-H, 100), 419(43), 374 (33), 323 (26), 308 (43), 295 (40), 280 (34), 250 (29), 236 (48), 222 (26), 169 (39), 155 (30), 129 (27), 99 (54), 91 (31), 86 (84), 79 (34), 75 (30).

EXAMPLE 2

The Preparation of the Compound of Formula (IV), (17α-Hydroxy-19-norpregna-4,9-diene-3,20-dione) From The Compound of Formula (IIIa)

300 grams of a 30% by weight dispersion of lithium metal in mineral oil (12.97 mol of Li) were placed in a 2.0 L addition funnel under argon. 759 mL of pentane were added to the addition funnel, and the lithium metal was allowed to migrate to the top. The lower pentane-mineral oil layer was carefully drained into a large flask. The addition funnel was fitted onto a 12.0 L, 3 neck reaction flask. The lithium metal was washed into the flask with 1,300 mL of THF. The flask was fitted with a stirring shaft having a glass paddle. 1,300 mL of a THF solution containing 500 g (1.88 mol) of di-t-butylbiphenyl (DBB) were added to the THF suspension of lithium using a metering pump. The resulting blue Li/DBB mixture was stirred at room temperature for 2 hours. After chilling the flask to −70° C., 2,400 mL of a THF solution containing 898 g of the compound of formula (IIIa) were added to the Li/DBB mixture at a rate designed to maintain the blue color throughout the addition. Upon completion of the addition, dichloroethane (400 mL) was added slowly to destroy excess anion-radical. 4,000 mL of 6N aqueous HCl were then added slowly, and the reaction mixture was allowed to warm to room temperature and was stirred overnight.

The reaction mixture was evaporated in vacuo to remove the THF, and the resulting aqueous mixture was extracted with methylene chloride. Following washes with water and brine, the methylene chloride extracts were combined and dried over sodium sulfate. Evaporation of the solvent gave a solid.

The solid was partitioned between hexanes and 90% methanol (3×2500 mL Hex/3×2500 mL, 90% MeOH). The combined methanol layers were evaporated to remove the methanol, and the aqueous mixture was extracted with methylene chloride.

The methylene chloride extracts were washed with water and brine combined, and dried over sodium sulfate. Evaporation of the solvent gave 572 g of a diketone, i.e., the compound of formula (IV) in 91% yield. The diketone of formula (IV) was a 4:1 mixture of 4,9(10)- and 5(10),9(11)-dienedione. The mixture was converted, without purification, to the 3,20-diketal (i.e., the compound of formula (V)) as described in Example 3. Evaporation of the hexane extracts allowed for the recovery of the DBB. NMR (CDCl$_3$) δ0.83 (s, 18-CH$_3$), 2.30 (s, 21-CH$_3$), 5.70 (br.s, C-4 H).

EXAMPLE 3

The Preparation of the Compound of Formula (V) (3,20-bis-Ethylenedioxy-17α-hydroxy-19-norpregna-5(10), 9(11)-diene) From the Compound of Formula (IV)

To 3,800 mL of a methylene chloride solution containing 543 g of the diketone of formula (IV) (1.73 mol) were added 540 mL of ethylene glycol (9.68 mol), 864 mL of distilled triethyl orthoformate (5.19 mol), and 21.6 g of p-toluenesulfonic acid monohydrate (0.11 mol) The mixture was stirred overnight at room temperature.

The mixture was diluted with 2,150 mL of saturated sodium bicarbonate solution and stirred for 10 minutes. The methylene chloride layer was washed with water (2×) and brine. The aqueous washes were extracted with additional methylene chloride. The methylene chloride extracts were combined and dried over sodium sulfate. The methylene chloride solution was concentrated to a thick syrup. Approximately 2,000 mL of methanol containing 0.5 vol % pyridine was drawn into the evaporation flask and the evaporative removal of the methylene chloride was continued. The flask was removed from the roto-vap, and additional methanol with 0.5 vol. % pyridine was added. The flask was chilled to 4° C. The solid obtained was collected by filtration, washed with cold methanol, and dried in vacuo overnight to give 432.5 g of the compound of formula (V) in 62% yield; m.p. 170–172° C. (CDCl$_3$) δ0.80 (s, 18-CH$_3$), 1.38 (s, 21-CH$_3$), 4.0 (m, 3,20-diketal), 5.60 (br.s, C-11 H). Anal. Cal'd for C$_{24}$H$_{34}$O$_5$: C, 71.61, H, 8.51 Found C, 71.53, H, 8.50.

EXAMPLE 4

The Preparation of the Compound of Formula (VI) (3,20-bis-Ethylenedioxy-17α-hydroxy-5α,10α-epoxy-19-norpreg-9(11)-ene) From the Compound of Formula (V)

A mixture of 261.5 g of hexafluoroacetone trihydrate (1.18 mol) in 2,500 mL of methylene chloride was chilled to 4° C. To this mixture were added 125 g of sodium phosphate dibasic (0.88 mol) and 238 mL of 30% hydrogen peroxide (210 mmol), and the mixture was stirred for 20 minutes at 4° C. 2,500 mL of a cold (4° C.) solution of methylene chloride containing 432.2 g of the diketal of formula (V) (1.08 mol) were added to the above mixture and stirred overnight at 4° C. The mixture was diluted with 3,000 mL of a 10 weight % sodium sulfite solution and stirred for 30 minutes. The layers were separated and the aqueous layer was extracted with additional methylene chloride. The methylene chloride extracts were washed with water and brine, combined, and dried over sodium sulfate. The solvent was evaporated, and the residue was taken up in 1,200 mL of ether. The ether solution was chilled to 4° C., and the resulting solid was collected by filtration, washed with ether, and dried in vacuo to give 176.8 g of pure 9,11-unsaturated 5α,10α-epoxide (i.e., the compound of formula (VI)) as white crystals; m.p. 188.5–191.5° C. FTIR (KBr, diffuse reflectance): $v_{max}$ 3510 (OH), 2947, 2887, 2669, 1649, 1469, 1438, 1369, 1326, 1220, 1186, 1132, 1109, 1084, 1066, 1047, 1004; NMR (CDCl$_3$) δ0.77(s, 18-CH$_3$), 1.35(s 21-CH$_3$), 6.04 (m, C-11 H of α-epoxide); MS (EI) m/z (relative intensity) 418 (H$^+$, 18), 400 (H$^+$-H$_2$O, 77), 293 (35), 141 (30), 131 (92), 115 (56), 87 (100). Anal. calc'd for C$_{24}$H$_{34}$O$_6$: C, 68.88; H, 8.19 Found: C, 68.70; H, 8.09.

EXAMPLE 5

The Preparation of the Compound of Formula (VII) (3,20-bis-Ethylenedioxy-5α,17α-dihydroxy-11β-(4-N,N-dimethylaminophenyl)-19-norpregn-9-ene) from the Compound of Formula (VI)

A dry 12-L, 3-neck flask equipped with a stir shaft, condenser, and argon inlet, was charged with 51.1 g of activated magnesium (2.10 mol). Several crystals of iodine and 10 mL of dibromoethane were added, followed by the addition of 1,000 mL of THF. While maintaining stirring, 2,000 mL of a THF solution containing 421.7 g of p-bromo-N,N-dimethylaniline (2.11 mol) were added at such a rate that a gentle reflux was maintained. Upon completion of the addition, the mixture was stirred for 1.5 hours and cooled to room temperature. 20.8 g of copper (I) chloride (0.21 mol) were added and stirred at room temperature for 30 minutes. 1,500 mL of a THF solution containing 176.3 g of the 9,11-unsaturated 5α,10α-epoxide of formula (VI) (0.42 mol) were added over 30 minutes. After stirring for 1 hour, the reaction was quenched with the slow addition of an ammonium chloride solution (approx. 800 g $NH_4Cl$/approx. 4,500 mL total volume) and stirred for 30 minutes. While stirring vigorously, air was bubbled through the mixture for 5–10 minutes to oxidize $Cu^I$ to $Cu^{II}$. The layers were allowed to separate. The upper THF layer was washed with 1,000 mL of 10% ammonium chloride solution. The THF layer was diluted with 4,500 mL of ether and washed with 10% by weight ammonium chloride (5×1,000 mL) and 2.0N ammonium hydroxide (5×1,000 mL). The THF/ether solution was washed with water and brine. After drying over sodium sulfate, the solvent was evaporated in vacuo. The residue obtained was diluted with ether, and the solid was collected by filtration, washed with ether, and dried in vacuo to give 179.7 g of the compound of formula (VII) in 79% yield as white crystals; mp=236°–240° C. dec. Extraction of all aqueous washes with ether gave an additional 6.8 g of the compound of formula (VII). A total of 186.5 g of the desired compound (VII) was obtained in 82% yield. FTIR (KBr, diffuse reflectance). $v_{max}$ 3573, 3543, 3087, 2976, 2945, 2874, 1612, 1516, 1484, 1447, 1484, 1396, 1371, 1340, 1238, 1214, 1128, 1190, 1100, 1076, 1052; NMR ($CDCl_3$) δ0.49 (s, 18-$CH_3$), 1.39 (s, 21-$CH_3$), 3.92 (br.m, 3,20-diketal), 4.20 (d, C-11 H), 6.70 and 7.16 (d, aromatic H); MS (EI) m/z (relative intensity): 539 ($M^+$, 83), 521 ($M^+$-$H_2O$, 57), 324 (21), 238 (26), 134 (10), 121 (30), 87 (100). Anal. calc'd. for $C_{32}H_{45}NO_6$ C, 71.21; H, 8.40; N, 2.60. Found C, 71.29; H, 8.35; N, 2.74.

EXAMPLE 6

The Preparation of the Compound of Formula (VIII) (11β-(4-N,N-Dimethylaminophenyl)-17α-hydroxy-19-norpregn-4,9-diene-3,20-dione) from the Compound of Formula (VII)

Argon was bubbled for 10 minutes through 3,250 mL of a 10:1 mixture of absolute ethanol and 8.5 vol. % sulfuric acid solution. 178.6 g of the compound of formula (VII) (0.33 mol) were added as a solid. The mixture was stirred, heated to reflux, and maintained at that temperature for 40 minutes. The reaction mixture was cooled in an ice bath, and the acid was neutralized by adding saturated sodium bicarbonate solution. The mixture was filtered, and the filtrate was evaporated in vacuo. The resulting aqueous mixture was diluted with 2,000 mL of water and extracted with methylene chloride. The methylene chloride extracts were washed with water and brine, combined, and dried over sodium sulfates Evaporation of the solvent gave 161.8 g of the compound of formula (VIII). The material was taken up in 1,350 mL of ether and set aside to crystallize. This procedure gave 128.3 g of the compound of formula (VIII) as an off-white solid in 90% yield, m.p.: softens at 103° C., foams at 125–128° C. FTIR (KBr, diffuse reflectance): $v_{max}$ 3448 (OH), 3074, 1709 (C=O), 1643, 1602 (conjugated-C=O), 1560, 1519, 1440; NMR ($CDCl_3$) δ0.44 (s, 18-$CH_3$), 2.24 (s, 21-$CH_3$), 2.90 (s, —N($CH_3$)$_2$), 4.38 (d, C-11 H), 5.78 (br. s, C-4 H), 6.67 and 7.02 (d, aromatic H): MS EI m/z (relative intensity) 433 ($M^+$, 35), 280(7), 134(21), 121(100) Anal. calc'd for $C_{28}H_{35}NO_3$:C, 77.56; H, 8.14; N, 3.23. Found C, 77.54; H, 7.98; N, 3.46.

EXAMPLE 7

The Preparation of the Compound of Formula (I) (17α-Acetoxy-11β-(4-N,N-dimethylaminophenyl)-19-norpregna-4,9-diene-3,20-dione) From the Compound of Formula (VIII)

340 mL of acetic acid (5.92 mol) were added to a well stirred mixture containing 834 mL of trifluoroacetic anhydride (5.92 mol) in 2,300 mL of methylene chloride under argon. After stirring for 30 minutes at room temperature, 51.3 g of p-toluenesulfonic acid (0.26 mol) were added, and the mixture was chilled to 0° C. 400 mL of a chilled (0° C.) methylene chloride solution containing 128.3 g of the compound of formula (VIII) (0.30 mol) were added, and the reaction mixture was stirred at 0° C. for 30 minutes. The reaction mixture was quenched with the cautious addition of a 4.5N potassium carbonate solution until the pH was in the range of 7.0–7.5. The reaction mixture was diluted with water and extracted with methylene chloride. The methylene chloride extracts were washed with water and brine, combined, and dried over sodium sulfate. Evaporation of the solvent gave the acetate of formula (I) as a thick syrup.

The above syrup was dissolved in 300 mL of isopropyl alcohol and evaporated. The dissolution and evaporation were repeated three times. Finally, the remaining solid, which retained isopropyl alcohol as solvent of recrystallization, was dissolved in ethyl acetate and evaporated to give a stable foam. The foam was quickly dissolved in ether, and this solution was set aside to crystallize. The solid that formed was collected by filtration, washed with ether, and dried in vacuo to yield 105.7 g of the compound of formula (I) as yellow crystals in 75% yield; m.p. 183–185° C. FTIR (KBr, diffuse reflectance): $v_{max}$2945, 1735 and 1714(—C=O), 1664 and 1661 (conjugated —C=O), 1563, 1518, 1441, 1351, 1305, 1252, 1203, 1171; NMR ($CDCl_3$) δ0.38 (s, 18-$CH_3$), 2.10 (s, 17-OAc), 2.14 (s, 21-$CH_3$), 2.92 (s, —N($CH_3$)$_2$), 4.44 (d, C-11 H), 5.83 (br. s, C-4 H), 6.71 and 7.07 (d, aromatic H); MS(EI) m/z (relative intensity) 475($M^+$, 41), 134(18), 121 (100). Analysis calculated for $C_{30}H_{37}NO_4$: C, 75.76; H, 7.84; N, 2.94. Found. C, 75.80; H 7.96; N, 3.09.

All of the references cited herein, including patents, patent applications, and publications, are hereby incorporated in their entireties by reference.

While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:
1. A method for preparing the compound of formula I

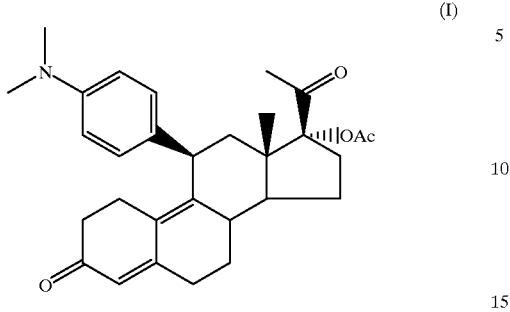

comprising protecting the hydroxyl group in the compound of formula II

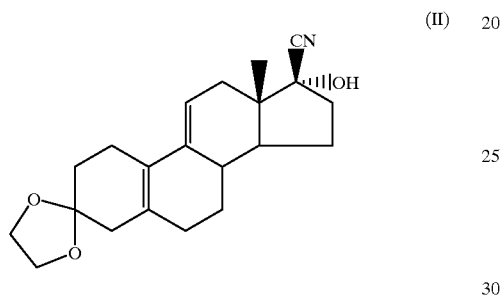

with protecting group B which comprises a halomethyl functional group to provide the compound of formula III

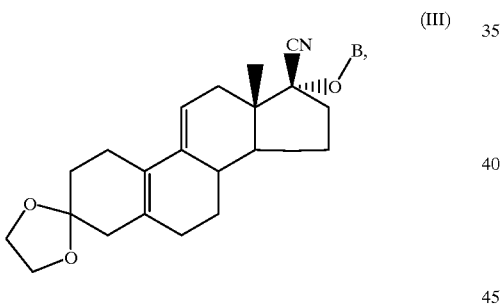

reacting the protected compound of formula III with an alkali or alkaline earth metal anion radical comprised of an alkali or alkaline earth metal and an anion radical and hydrolyzing the resulting compound to provide the compound of formula IV

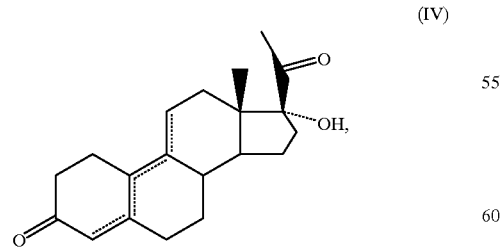

ketalizing the carbonyl groups of the compound of formula IV to provide the compound of formula V

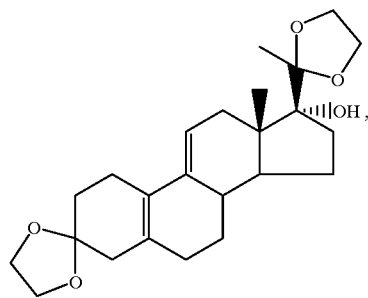

epoxidizing the compound of formula V to provide the 9,11-unsaturated 5α,10α-epoxide of formula VI

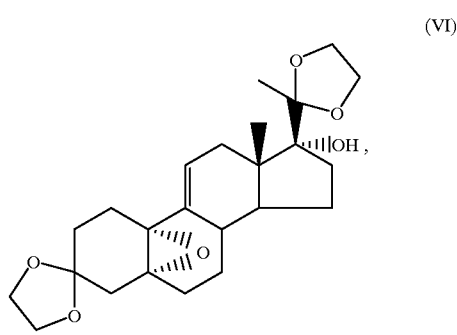

introducing into the axial position of $C_{11}$ of the compound of formula VI a N,N-dimethylamino-phenyl functional group by the use of a reagent consisting essentially of a cuprous halide and the Grignard reagent (Me)$_2NC_8H_1MgCl$ with concomitant epoxide ring opening, quenching the Grignard reaction mixture with an ammonium salt, and oxidizing the cuprous halide to cupric halide, to provide the compound of formula VII

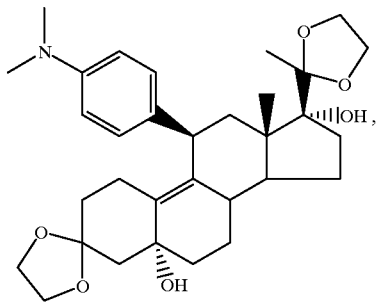

deketalizing and dehydrating the compound of formula VII to provide the compound of formula VIII

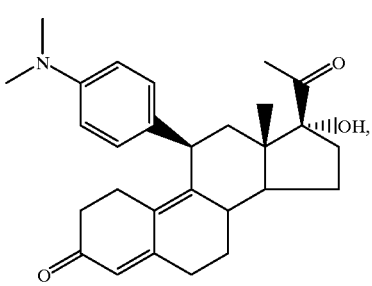

(VIII)

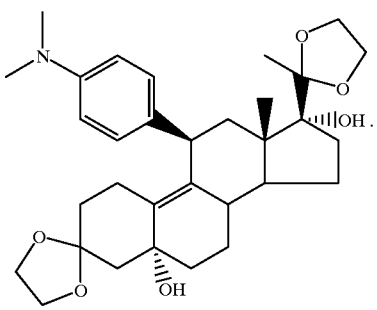

(VII)

purifying the compound of formula VIII by crystallization, and acetylating the compound of formula VIII to provide the compound of formula I.

2. A method for preparing a crystalline form of the 5α,10α-epoxy compound of formula VI

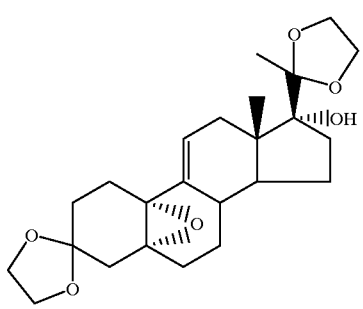

(VI)

comprising epoxidizing the compound of formula V

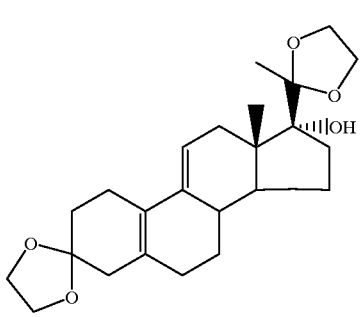

(V)

with an adduct formed from the reaction of a hexahalogenated acetone and a peroxide in the presence of an inorganic phosphate and purifying the resulting product by crystallization from a medium consisting essentially of ether to provide a crystalline form of the 5α,10α-compound of formula VI.

3. The method according to claim 2, wherein the inorganic phosphate is anhydrous disodium phosphate and the hexahalogenated acetone is hexafluoroacetone.

4. The method of claim 2, wherein said Grignard reagent is prepared from a N,N-dimethylaniline and magnesium in the presence of cuprous chloride followed by quenching with ammonium chloride to provide the compound of formula VII 5. The method of claim 4, wherein the cuprous chloride is provided in less than an equimolar amount as compared to the epoxide.

6. The method of claim 5, wherein the Grignard reagent is prepared from the reaction of p-bromo-N,N-dimethylaniline and magnesium in the presence of cuprous chloride.

7. The method of claim 6, wherein the Grignard reagent is provided in a molar amount which is no greater than about five times the molar amount of the epoxide.

8. The method of claim 4, further comprising converting the compound of formula VII to a crystalline form of the compound having a melting point of 236° C. to 240° C.

9. The method of claim 8, further comprising deketalizing and dehydrating the compound of formula VII to provide the compound of formula VIII

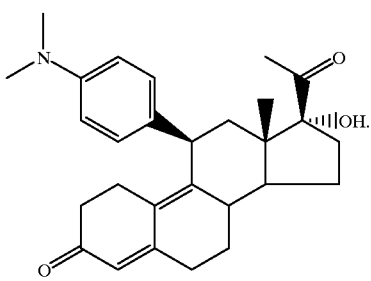

(VIII)

10. The method of claim 9, further comprising converting the compound of formula VIII to a crystalline form of the compound which softens at 103° C. and foams at 125° C. to 128° C.

11. The method of claim 10, further comprising reacting the compound of formula VIII with an acetylating agent to provide the compound of formula I

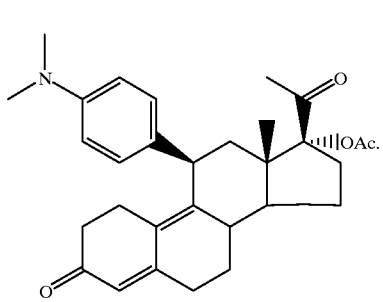

(I)

12. The method of claim 11, further comprising converting the compound of formula I to a crystalline form of the compound which has a melting point of 183° C. to 185° C.

13. The method according to claim 12, wherein the acetylating agent is a mixture prepared from trifluoroacetic anhydride, acetic acid, and p-toluenesulfonic acid.

14. The method according to claim 2, wherein the compound of formula V is prepared by protecting the hydroxyl group in the compound of formula II

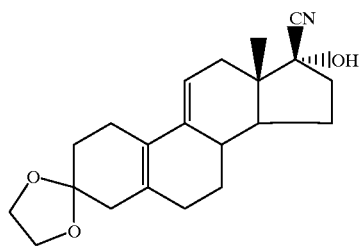
(II)

with chloromethyldimethylchlorosilane to provide the compound of formula IIIa

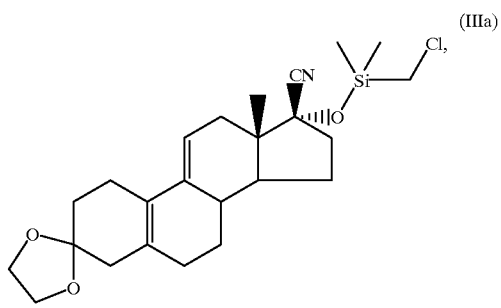
(IIIa)

forming a crystalline form of the compound of formula IIIa having a melting point of 80° C. and 82° C., reacting the compound of formula IIIa with an alkali metal anion radical of 4,4'-di-tert-butylbiphenyl and hydrolyzing the ketal to provide the compound of formula IV

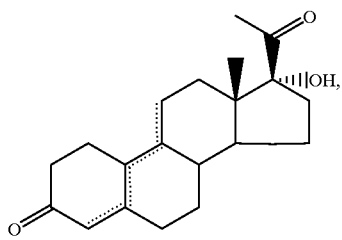
(IV)

and ketalizing the carbonyl groups of the compound of formula IV to provide the compound of formula V

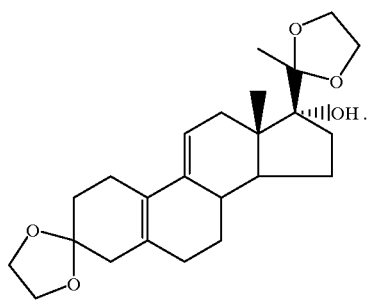
(V)

15. A method for preparing the compound of formula I

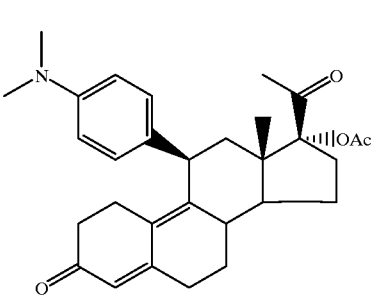
(I)

comprising
(a) deketalizing and dehydrating the compound of formula VII

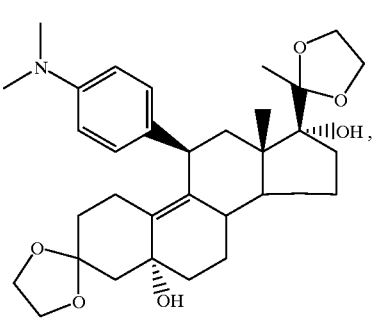
(VII)

to form the compound of formula VIII

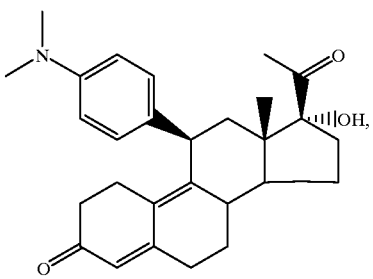
(VIII)

(b) isolating the compound of formula VIII formed in step (a) by crystallization, and
(c) acetylating the compound of formula VIII isolated in step (b) by the use of trifluoroacetic anhydride, acetic acid, and p-toluenesulfonic acid to provide the compound of formula I

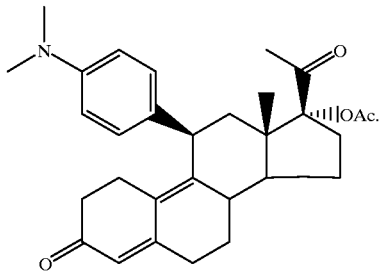
(I)

16. The method according to claim 15, wherein the isolation of step (b) is completed by crystallizing the compound of formula VIII from ether.

17. The method of claim 1, wherein said ammonium salt is ammonium chloride.

18. The method of claim 1, wherein said cuprous halide is oxidized by air.

19. A method for preparing the compound of formula I

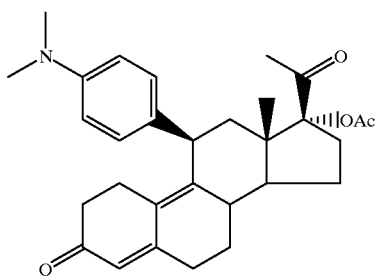
(I)

comprising protecting the hydroxyl group in the compound of formula II

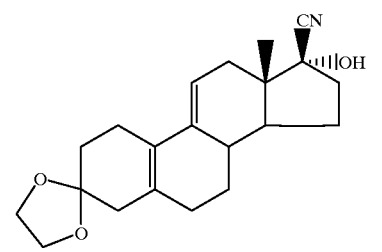
(II)

with protecting group B which comprises a halomethyl functional group to provide the compound of formula III

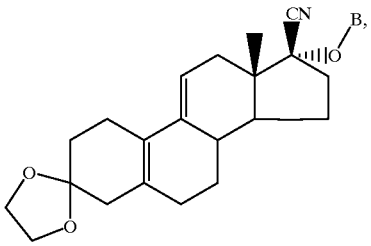
(III)

reacting the protected compound of formula III with an alkali or alkaline earth metal anion radical comprised of an alkali or alkaline earth metal and an anion radical and hydrolyzing the resulting compound to provide the compound of formula IV

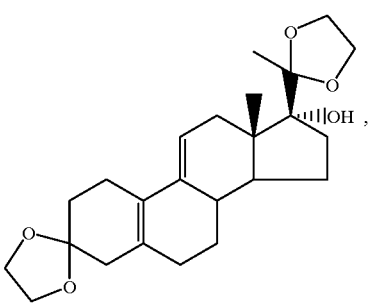
(IV)

ketalizing the carbonyl groups of the compound of formula IV to provide the compound of formula V

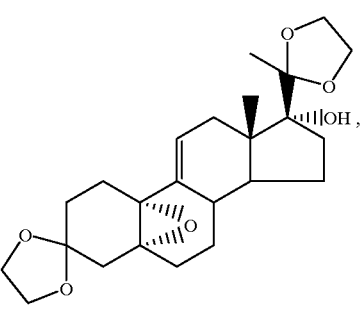
(V)

epoxidizing the compound of formula V to provide the 9,11-unsaturated 5α,10α-epoxide of formula VI

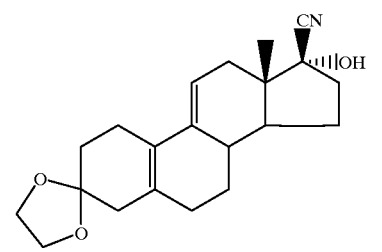
(VI)

introducing into the axial position of $C_{11}$ of the compound of formula VI a N,N-dimethylamino-phenyl functional group by the use of a reagent consisting essentially of cuprous chloride and the Grignard reagent $(Me)_2NC_8H_4MgCl$ with concomitant epoxide ring opening, quenching the Grignard reaction mixture with ammonium chloride, and oxidizing the cuprous chloride to cupric chloride, to provide the compound of formula VII

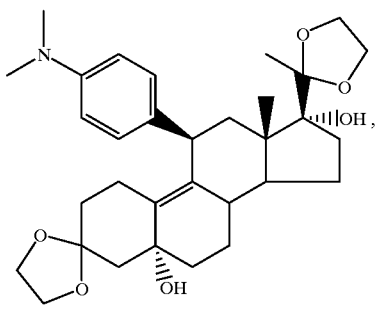

(VII)

deketalizing and dehydrating the compound of formula VII to provide the compound of formula VIII

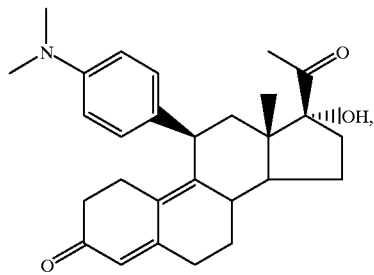

(VIII)

purifying the compound of formula VIII by crystallization, and acetylating the compound of formula VIII to provide the compound of formula I.

\* \* \* \* \*